(12) United States Patent
Fawzi et al.

(10) Patent No.: US 7,504,394 B2
(45) Date of Patent: Mar. 17, 2009

(54) BAZEDOXIFENE ASCORBATE

(75) Inventors: Mahdi B. Fawzi, Morristown, NJ (US); Kadum A. Ali, Congers, NY (US); Syed M. Shah, East Hanover, NJ (US)

(73) Assignee: Wyeth, Madison, NJ (US)

( * ) Notice: Subject to any disclaimer, the term of this patent is extended or adjusted under 35 U.S.C. 154(b) by 590 days.

(21) Appl. No.: 11/100,902

(22) Filed: Apr. 7, 2005

(65) Prior Publication Data

US 2005/0227964 A1    Oct. 13, 2005

Related U.S. Application Data

(60) Provisional application No. 60/560,454, filed on Apr. 8, 2004.

(51) Int. Cl.
*A61P 19/08* (2006.01)
*A61K 31/55* (2006.01)
*C07D 403/00* (2006.01)

(52) U.S. Cl. .................. 514/217.08; 540/602

(58) Field of Classification Search ............ 514/217.08; 540/602
See application file for complete search history.

(56) References Cited

U.S. PATENT DOCUMENTS

| 4,133,814 A | 1/1979 | Jones et al. |
| 4,418,068 A | 11/1983 | Jones et al. |
| 5,332,727 A | 7/1994 | Birkmayer |
| 5,510,358 A | 4/1996 | Palkowitz |
| 5,747,510 A | 5/1998 | Draper |
| 5,780,497 A | 7/1998 | Miller et al. |
| 5,811,120 A | 9/1998 | Gibson et al. |
| 5,880,137 A | 3/1999 | Miller et al. |
| 5,919,800 A | 7/1999 | Palkowitz |
| 5,998,402 A | 12/1999 | Miller et al. |
| 6,242,605 B1 | 6/2001 | Raveendranath et al. |
| 6,479,535 B1 | 11/2002 | Pickar et al. |
| 2002/0031548 A1 | 3/2002 | Benjamin et al. |

FOREIGN PATENT DOCUMENTS

| EP | 802183 | 10/1997 |
| EP | 802184 | 10/1997 |
| EP | 1336602 | 8/2003 |
| WO | WO 96/21656 | 7/1996 |
| WO | WO 99/19293 | 4/1999 |
| WO | WO 02/03987 | 1/2002 |

OTHER PUBLICATIONS

Miller, et al., "Design, Synthesis, and Preclinical Characterization of Novel, Highly Selective Indole Estrogens," *J. Med. Chem.* (2001) 44 (11):1654-1657 and supporting information.
Miller, et al., Drugs of the Future (2002) 27(2):117.
Greenberger, et al., "A New Antiestrogen, 2-(4-Hydroxy-phenyl)-3-methyl-1-[4-(2-piperidin-1-yl-ethoxy)-benzyl]-1H-indol-5-ol hydrochloride (ERA-923), Inhibits the Growth of Tamoxifen-sensitive and -resistant Tumors and Is Devoid of Uterotopic Effects in Mice and Rats," *Clinical Cancer Research* (2001) 7:3166-3177.
Leuner, C., et al., "Improving Drug Solubility for Oral Delivery Using Solid Dispersions," *European Journal of Pharmaceutics and Biopharmaceutics* 50 (2000) 47-60.
Passerini, N., "Preparation and Characterisation of Ibuprofen-Poloxamer 188 Granules Obtained by Melt Granulation," *European Journal of Pharmaceutical Sciences* 15 (2002) 71-78.
Remington's Pharmaceutical Sciences, 17th Ed., Mac Publishing Company, Easton, PA, pp. 1012-1013, 1021-1022, 1278 (1985).

*Primary Examiner*—Brenda L Coleman
(74) *Attorney, Agent, or Firm*—Wilmer Cutler Pickering Hale and Dorr LLP

(57) ABSTRACT

The present invention is directed to bazedoxifene ascorbate, compositions containing the same, dispersions thereof, preparations thereof, and uses thereof.

32 Claims, No Drawings

BAZEDOXIFENE ASCORBATE

CROSS REFERENCE TO RELATED APPLICATIONS

This application claims the benefit of U.S. Ser. No. 60/560,454, filed Apr. 8, 2004, the disclosure of which is incorporated herein by reference in its entirety.

FIELD OF THE INVENTION

The present invention relates to the ascorbic acid salt of the selective estrogen receptor modulator 1-[4-(2-azepan-1-yl-ethoxy)-benzyl]-2-(4-hydroxy-phenyl)-3-methyl-1H-indol-5-ol (bazedoxifene), as well as compositions thereof and uses thereof.

BACKGROUND OF THE INVENTION

Bazedoxifene (1-[4-(2-azepan-1-yl-ethoxy)-benzyl]-2-(4-hydroxy-phenyl)-3-methyl-1H-indol-5-ol; or bazedoxifene free base), having the chemical formula shown below:

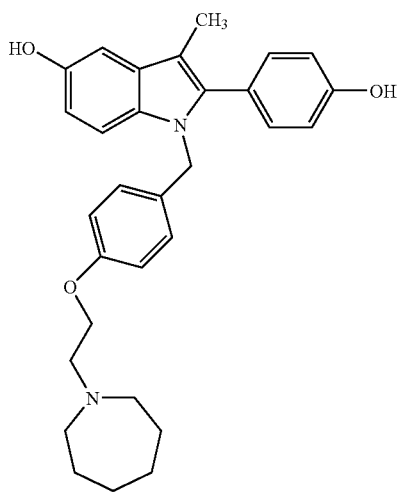

belongs to the class of drugs typically referred to as selective estrogen receptor modulators (SERMs). Consistent with its classification, bazedoxifene and its salts demonstrate affinity for estrogen receptors (ER) but show tissue selective estrogenic effects. For example, bazedoxifene acetate demonstrates little or no stimulation of uterine response in preclinical models of uterine stimulation. Conversely, bazedoxifene acetate demonstrates an estrogen agonist-like effect in preventing bone loss and reducing cholesterol in an ovariectomized rat model of osteopenia. In an MCF-7 cell line (human breast cancer cell line), bazedoxifene acetate behaves as an estrogen antagonist. These data demonstrate that bazedoxifene is estrogenic on bone and cardiovascular lipid parameters and antiestrogenic on uterine and mammary tissue and thus has the potential for treating a number of different disease or disease-like states wherein the estrogen receptor is involved.

U.S. Pat. Nos. 5,998,402 and 6,479,535 report the preparation of bazedoxifene and salts thereof. The synthetic preparation of bazedoxifene and its salts has also appeared in the general literature. See, for example, Miller et al., *J. Med. Chem.*, 2001, 44, 1654-1657.

Further description of the drug's biological activity has appeared in the general literature as well (e.g. Miller, et al. *Drugs of the Future,* 2002, 27(2), 117-121).

Because drug formulations showing, for example, improved stability, solubility, and bioavailability are consistently sought, there is an ongoing need for new forms of existing drug molecules. The ascorbic acid salt of bazedoxifene and compositions containing the same described herein helps meet these and other needs.

SUMMARY OF THE INVENTION

The present invention provides an ascorbic acid salt of bazedoxifene and compositions comprising the same.

The present invention further provides methods of preparing bazedoxifene ascorbate comprising combining bazedoxifene free base and ascorbic acid.

The present invention further provides solid dispersions comprising bazedoxifene ascorbate dispersed in a dispersing agent.

The present invention further provides methods of preparing solid dispersions of bazedoxifene ascorbate, comprising: a) combining bazedoxifene ascorbate and a dispersing agent in solution; and b) removing solvent to yield the solid dispersion.

The present invention further provides methods of preparing solid dispersions of bazedoxifene ascorbate, comprising: a) combining bazedoxifene ascorbate with melted dispersing agent to form a liquid mixture; and b) solidifying the liquid mixture to form the solid dispersion.

The present invention further provides methods of treating a mammal having a disease or syndrome associated with estrogen deficiency or excess of estrogen comprising administering to the mammal a therapeutically effective amount of bazedoxifene ascorbate.

The present invention further provides methods of treating a mammal having a disease or disorder associated with proliferation or abnormal development of endometrial tissues comprising administering to the mammal a therapeutically effective amount of bazedoxifene ascorbate.

The present invention further provides methods of lowering cholesterol in a mammal comprising administering to the mammal a therapeutically effective amount of bazedoxifene ascorbate.

The present invention further provides methods of inhibiting bone loss in a mammal comprising administering to the mammal a therapeutically effective amount of bazedoxifene ascorbate.

The present invention further provides methods of treating breast cancer in a mammal comprising administering to the mammal a therapeutically effective amount of bazedoxifene ascorbate.

The present invention further provides methods of treating postmenopausal woman for one or more vasomotor disturbances comprising administering to the postmenopausal woman a therapeutically effective amount of bazedoxifene ascorbate.

DETAILED DESCRIPTION

The present invention provides, inter alia, ascorbic acid salts of bazedoxifene, and solid dispersions and compositions thereof having improved properties relating to stability solubility, bioavailability and the like. For example, bazedoxifene ascorbate incorporates the antioxidant properties of ascorbic acid which can help resist decomposition (e.g., by oxidation) and prolong shelf-life. Bazedoxifene ascorbate also shows improved solubility compared with other forms of bazedoxifene which can result in increased bioavailability and lower dosages.

Bazedoxifene ascorbate can be characterized as an acid addition salt of bazedoxifene containing at least about one ascorbic acid molecule to every bazedoxifene molecule. For example, bazedoxifene ascorbate is characterized as having about a 1:1 molar ratio of bazedoxifene to ascorbic acid. In some embodiments, the bazedoxifene ascorbate salt of the invention can be amorphous, crystalline, other solid form or a mixture thereof. In further embodiments, the bazedoxifene ascorbate salt can be anhydrous, hydrated (e.g., hemi-, mono-, di-hydrated, etc.), solvated or a mixture of two or more thereof.

Bazedoxifene ascorbate can be prepared by any suitable method resulting in formation the salt. In some embodiments, the bazedoxifene ascorbate is formed by combining bazedoxifene free base and ascorbic acid. For example, bazedoxifene free base and ascorbic acid can be combined in about equimolar amounts. The combining can be optionally carried out in a solvent in which at least one of bazedoxifene acetate and ascorbic acid has at least some solubility. For example, bazedoxifene free base and ascorbic acid can be dissolved together in a solvent, and then the solvent can be removed to yield the desired salt. Suitable solvents for forming the salts of the invention include organic solvents such as, for example, alcohols, ethers, hydrocarbons, halogenated hydrocarbons, nitriles, mixtures thereof, and the like. In some embodiments, the organic solvent is a volatile solvent such as methanol, ethanol, isopropanol, diethyl ether, pentane, hexane, benzene, dichloromethane, acetonitrile, mixtures thereof and the like. In some embodiments, the organic solvent is an alcohol such as methanol, ethanol, n-propanol, ispropanol, mixtures thereof and the like. In some embodiments, the organic solvent is ethanol.

Bazedoxifene ascorbate can also be prepared by replacing the anion of a different salt of bazedoxifene with ascorbate. For example, bazedoxifene acetate or other bazedoxifene salt can be treated with ascorbic acid or an ascorbate salt to form bazedoxifene ascorbate. This anion-replacement reaction can be optionally carried out in a solvent, such as an organic solvent described herein.

The present invention further provides solid dispersions of bazedoxifene ascorbate. The solid dispersions of the invention have increased solubility and bioavailability compared with, for example, bazedoxifene free base, crystalline bazedoxifene acetate and other salt forms of bazedoxifene. The increased bioavailability associated with solid dispersions has numerous advantages including allowing for administration of lower dosages, thereby lessening the chance for adverse side effects and reducing subject variability.

The compositions of the invention contain, for example, bazedoxifene ascorbate dispersed in a dispersing agent. In some embodiments, the weight ratio of bazedoxifene ascorbate to dispersing agent is about 1:99 to about 99:1. In some embodiments, the weight ratio of bazedoxifene ascorbate to dispersing agent is about 1:99 to about 75:25 or about 1:99 to about 60:40. In further embodiments, the weight ratio of bazedoxifene ascorbate to dispersing agent is about 1:99 to about 15:85; about 1:99 to about 10:90; or about 1:99 to about 5:95. In further embodiments, the weight ratio of bazedoxifene ascorbate to dispersing agent is about 5:95. In further embodiments, the weight ratio of bazedoxifene ascorbate to dispersing agent is about 25:75 to about 75:25, about 40:60 to about 60:40 or about 1:1. In some embodiments, the weight ratio of bazedoxifene ascorbate to dispersing agent is about 1:1.

The "dispersing agent," as used herein, refers to any substance or mixture of substances that acts as a dispersing medium for molecules/particles of bazedoxifene ascorbate. The dispersing agent is typically composed of a pharmaceutically acceptable substance that does not substantially interfere with the pharmaceutical action of bazedoxifene ascorbate. The phrase "pharmaceutically acceptable" is employed herein to refer to those substances which are, within the scope of sound medical judgment, suitable for use in contact with the tissues of human beings and animals without excessive toxicity, irritation, allergic response, or other problem or complication, commensurate with a reasonable benefit/risk ratio. In some embodiments, the dispersing agent is a solid at room temperature (e.g., about 22° C.). In further embodiments, the dispersing agent melts at a temperature between about 30 and 100° C. In further embodiments, the dispersing agent is soluble in an organic solvent.

Non-limiting examples of dispersing agents include polymers such as celluloses (e.g., carboxymethylcelluloses, methylcelluloses, hydroxypropylcelluloses, hydroxypropylmethylcelluloses); hyaluronates; alginates; polysaccharides, heteropolysaccharides (pectins); poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines (lecithins); miglyols; polylactic acid; polyhydroxybutyric acid; mixtures thereof, copolymers thereof, derivatives thereof, and the like. Further example dispersing agents include copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

In some embodiments, the dispersing agent contains polyvinylpyrrolidone (PVP) or derivative thereof. PVP is a polyamide that forms complexes with a wide variety of substances and is considered to be chemically and physiologically inert. Examples of suitable PVPs include polyvinylpyrrolidones having an average molecular weight from about 10,000 to about 50,000. In some embodiments, the polyvinylpyrrolidone has an average molecular weight of about 10,000 to about 20,000. In further embodiments, the polyvinylpyrrolidone has a molecular weight of about 15,000 to about 20,000. An example of a suitable PVP is PVP K-17 (PLASDONE povidone, ISP Technologies, Ltd.). In some embodiments, the dispersing agent consists essentially of PVP or derivative thereof.

In some embodiments, the dispersing agent contains a block co-polymer of ethylene and propylene glycol, often referred to as a Poloxamer. Examples of suitable Poloxamers include Poloxamer 188 (LUTROL F 68, BASF), Poloxamer 407 (LUTROL F 127, BASF), and the like. In some embodiments, the dispersing agent is Poloxamer 188.

In some embodiments, the dispersing agent contains a polyethylene glycol (PEG). Suitable PEGs include PEG 200, 300, 400, 600, 1000, 1450, 3350, 4000, 6000, 8000, 10000, 20000, mixtures thereof and the like. In some embodiments, the dispersing agent is PEG 1450.

The bazedoxifene ascorbate dispersions of the invention can be made by any of numerous methods that result in, for example, a solid dispersion of amorphous bazedoxifene ascorbate. In an example method, bazedoxifene ascorbate (in any form, e.g., crystalline, amorphous, etc.) and the dispersing agent can be dissolved in a dispersing solvent (together, or separately and then combined) in the weight ratio desired and then the dispersing solvent is removed to yield the desired solid dispersion. The dispersing solvent can be an aqueous solvent or organic solvent. Suitable organic solvents include alcohols, ethers, hydrocarbons, halogenated hydrocarbons, nitrites, mixtures thereof, and the like. In some embodiments, the organic solvent is a volatile solvent such as methanol, ethanol, isopropanol, diethyl ether, pentane, hexane, benzene, dichloromethane, acetonitrile, mixtures thereof and the like. In some embodiments, the organic solvent is an alcohol such as methanol, ethanol, n-propanol, ispropanol, mixtures thereof and the like. In some embodiments, the organic solvent is ethanol.

In another example, bazedoxifene ascorbate and dispersing agent can be combined in the desired weight ratio when either or both the bazedoxifene ascorbate and dispersing agent is (are) in liquid form (e.g., a melt); and then the liquid mixture is solidified to form the desired solid dispersion. According to such embodiments, the bazedoxifene ascorbate and dispersing agent can be combined when at least one of the bazedoxifene ascorbate and dispersing agent is melted. The resulting mixture is then solidified by cooling to a temperature sufficient to solidify the mixture. In some embodiments, the mixture is cooled to about 25° C. or below. In some embodiments, bazedoxifene ascorbate is combined with melted dispersing agent and the resulting mixture cooled to a temperature below the melting point of the mixture to form the solid dispersion. In further embodiments, the dispersing agent is heated to a temperature between about 30 and 200° C., between about 30 and 150° C. or between about 30 and 100° C., which is a temperature that is at or above the melting point of the dispersing agent. In further embodiments, the dispersing agent is heated to a temperature above about 30, above about 40, above about 50, above about 60, above about 70, above about 80 or above about 90° C. These and other methods are routine techniques suitable for the preparation of the bazedoxifene ascorbate dispersions of the invention.

Dosage and Formulation

The salt forms and solid dispersions described herein can be formulated for administration to a patient in any of a variety of ways. In some embodiments, the salt forms and solid dispersions can be administered alone, i.e., without the addition of excipients or other additives. For example, solid dosage forms (e.g., tablets, capsules etc.) containing greater than about 95%, greater than about 98%, or greater than about 99% (by weight) of a salt form or solid dispersion described herein can be directly administered to a patient.

In some embodiments, the salt forms or solid dispersions are combined with one or more pharmaceutically acceptable carriers (excipients) to form a pharmaceutical composition for administration to a patient. The composition can contain any amount of salt form or solid dispersion. In some embodiments, the compositions contains about 1 to about 99% by weight of the salt form or solid dispersion. In further embodiments, the composition contains about 1 to about 50% by weight of the salt form or solid dispersion. In yet further embodiments, the composition contains about 1 to about 30% by weight of the salt form or solid dispersion. In yet further embodiments, the composition contains about 1 to about 20% by weight of the salt form or solid dispersion. In yet further embodiments, the composition contains about 1 to about 10% by weight of the salt form or solid dispersion.

Formulations containing the present salt forms and/or solid dispersions can be administered in daily doses ranging from 0.1 mg to 1000 mg of bazedoxifene ascorbate to a person in need. Preferred dose ranges vary from 10 mg/day to about 600 mg/day, more preferably from 10 mg/day to about 60 mg/day. The dosing can be either in a single dose or two or more divided doses per day. Such doses can be administered in any manner that facilitates the compound's entry into the bloodstream including orally, via implants, parenterally, vaginally, rectally, and transdermally.

Transdermal administrations include all administrations across the surface of the body and the inner linings of body passages including epithelial and mucosal tissues. Such administration may be in the form of a lotion, cream, colloid, foam, patch, suspension, and the like.

Oral formulations containing the present salt forms or solid dispersions can comprise any conventionally used oral forms, including tablets, capsules, buccal forms, troches, lozenges and oral liquids, suspensions, and the like. Capsules or tablets of containing the present solid dispersion can also be combined with mixtures of other active compounds or inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Tablet formulations can be made by conventional compression, wet granulation, or dry granulation methods and utilize pharmaceutically acceptable diluents (fillers), binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations used herein may utilize standard delay or time release formulations or spansules. Suppository formulations may be made from traditional materials, including cocoa butter, with or without the addition of waxes to alter the suppositories melting point, and glycerin. Water soluble suppository bases, such as polyethylene glycols of various molecular weights, may also be used.

Film coatings useful with the present formulations are known in the art and generally consist of a polymer (usually a cellulosic type of polymer), a colorant and a plasticizer. Additional ingredients such as wetting agents, sugars, flavors, oils and lubricants can be included in film coating formulations to impart certain characteristics to the film coat. The compositions and formulations herein may also be combined and processed as a solid, then placed in a capsule form, such as a gelatin capsule.

The filler or diluent can comprise any substance known in the art that is useful for the preparation of solid oral formulations. Pharmaceutically acceptable fillers can be selected from, for example, lactose, microcrystalline cellulose, sucrose, mannitol, calcium phosphate, calcium carbonate, powdered cellulose, maltodextrin, sorbitol, starch, xylitol, and the like.

The present formulations can also include disintegrant agents. These disintegrants can be selected from those known in the art, including pregelatinized starch, sodium starch glycolate and the like. Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.). The disintegrant(s) useful herein can comprise from about 4% to about 40% of the composition by weight, preferably from about 15% to about 35%, more preferably from about 20% to about 35%.

Some components can have multiple functions in the formulations of this invention, acting e.g. as both a filler and a disintegrant, and its function in a specific formulation may be singular even though its properties may allow multiple functionality.

The pharmaceutical formulations and excipient systems herein can also contain an antioxidant or a mixture of antioxidants, such as ascorbic acid. Other antioxidants which can be used include sodium ascorbate and ascorbyl palmitate, optionally in conjunction with an amount of ascorbic acid. An example range for the antioxidant(s) is from about 0.05% to about 15% by weight, from about 0.5% to about 15% by weight, or from about 0.5% to about 5% by weight. In some embodiments, the pharmaceutical formulations contain substantially no antioxidant.

Pharmaceutical compositions of bazedoxifene ascorbate can also be formulated with steroidal estrogens, such as conjugated estrogens, USP. The amount of bazedoxifene ascorbate used in the formulation can be adjusted according to the particular solid dispersion used, the amount and type of steroidal estrogen in the formulation as well as the particular therapeutic indication being considered. In general, the bazedoxifene ascorbate can be used in an amount sufficient to antagonize the effect of the particular estrogen to the level desired. The dose range of conjugated estrogens can be from about 0.3 mg to about 2.5 mg, about 0.3 mg to about 1.25 mg, or about 0.3 mg to about 0.625 mg. An example range for amount of bazedoxifene ascorbate in a combination formulation is about 10 mg to about 40 mg. For the steroidal estrogen mestranol, a daily dosage can be from about 1 μG to about 150 μG, and for ethynyl estradiol a daily dosage of from about 1 μG to 300 μG can be used. In some embodiments, the daily dose is between about 2 μG and about 150 μG.

An example oral formulation contains the present salt form or solid dispersion and the following excipient systems:

a) a filler and disintegrant together comprising from about 1% to about 99% by weight (wt) of the total formulation, preferably between about 20% and about 85% of the formulation, of which from about 4% to about 45% by weight of the total formulation; and b) a lubricant comprising from about 0.2% to about 15% of the composition (wt), where the lubricant is magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parrafins, hydrogenated vegetable oils, leucine, polyethylene glycols, metallic lauryl sulfates or sodium chloride.

The percentages listed above for the filler, disintegrant, and lubricants are based on final pharmaceutical composition. The remainder of the final composition are comprised of the salt form or solid dispersion and a pharmaceutically acceptable surface covering, such as a coating or capsule, as described herein. In some embodiments of this invention, the salt form or solid dispersion comprises from about 1% to about 99%, about 10 to about 95%, or about 20 to about 90% by weight, of the final composition; and the coating or capsule comprises up to about 8%, by weight, of the formulation.

Additional numerous various excipients, dosage forms, dispersing agents and the like that are suitable for use in connection with the salt forms of the invention are known in the art and described in, for example, *Remington's Pharmaceutical Sciences,* 17th ed., Mack Publishing Company, Easton, Pa., 1985, which is incorporated herein by reference in its entirety.

Methods

As described in U.S. Pat. No. 5,998,402, bazedoxifene and salts thereof are selective estrogen agonists with affinity for the estrogen receptor. Unlike other types of estrogen agonists, bazedoxifene and salts thereof are antiestrogenic in the uterus and can antagonize the trophic effects of estrogen agonists in uterine tissues. Accordingly, the salt forms and solid dispersions of the invention, and compositions containing the same, can find many uses related to treating or preventing disease states or syndromes associated with an estrogen deficiency or an excess of estrogen. They may also be used in methods of treatment for diseases or disorders which result from proliferation or abnormal development, actions or growth of endometrial or endometrial-like tissues.

Bazedoxifene ascorbate has the ability to behave like an estrogen agonist by lowering cholesterol and preventing bone loss. Accordingly, the salt form or solid dispersion of the invention is useful for treating many maladies which result from estrogen effects and estrogen excess or deficiency including osteoporosis, prostatic hypertrophy, male pattern baldness, vaginal and skin atrophy, acne, dysfunctional uterine bleeding, endometrial polyps, benign breast disease, uterine leiomyomas, adenomyosis, ovarian cancer, infertility, breast cancer, endometriosis, endometrial cancer, polycystic ovary syndrome, cardiovascular disease, contraception, Alzheimer's disease, cognitive decline and other CNS disorders, as well as certain cancers including melanoma, prostrate cancer, cancers of the colon, CNS cancers, among others. Additionally, the solid dispersion can be used for contraception in pre-menopausal women, as well as hormone replacement therapy in post-menopausal women (such as for treating vasomotor disturbances such as hot flush) or in other estrogen deficiency states where estrogen supplementation would be beneficial. It can also be used in disease states where amenorrhea is advantageous, such as leukemia, endometrial ablations, chronic renal or hepatic disease or coagulation diseases or disorders.

The salt forms and solid dispersions of the invention can also be used in methods of treatment for and prevention of bone loss, which can result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using the solid dispersion in individuals with bone fractures, defective bone structures, and those receiving bone-related surgeries and/or the implantation of prosthesis. In addition to the problems described above, the solid dispersion can be used in treatments for osteoarthritis, hypocalcemia, hypercalcemia, Paget's disease, osteomalacia, osteohalisteresis, multiple myeloma and other forms of cancer having deleterious effects on bone tissues.

Methods of treating the diseases and syndromes listed herein are understood to involve administering to an individual in need of such treatment a therapeutically effective amount of the salt form or solid dispersion of the invention, or composition containing the same. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of Bazedoxifene Ascorbate

Synthesis 1

To a solution of 0.0713 g of ascorbic acid (crystalline powder) in 3 mL of ethanol heated on a water bath to 70° C. then cooled to about 40° C., was added with mixing 0.2001 g of bazedoxifene free base. The resulting suspension was heated to about 50° C. for 10 min forming a colorless solution which was cooled to room temperature. A faint yellow liquid layer formed at the base of the reaction vial.

2 mL of anhydrous ether was added to the cooled mixture to form a faint yellow precipitate. The supernatant liquid was decanted and the pasty precipitate was triturated with ether (2×1 mL) to form a creamy powder of about 0.1628 g of bazedoxifene ascorbate. The powder was kept in the dark and flushed with nitrogen in a closed container.

Synthesis 2

A solution of 0.7494 g (0.0042499 mole) of ascorbic acid (crystalline powder) in 32 mL of ethanol with stirring (magnetic stirrer) was heated to 70° C. until all solids were dissolved. The solution was cooled to 50° C. To the cooled solution, 2.04 g (0.0042499 mole) of bazedoxifene free base was added at once, stirred, and heated 3 hours at 60° C. forming a clear yellow-brown solution. The reaction was checked by HPLC with UV detection at 220 nm for bazedoxifene and 245 nm and 265 nm for ascorbic acid.

The resulting clear solution was cooled and solvents were evaporated under reduced pressure to dryness to give yellow-brown solid. Monitoring by HPLC showed that reaction progression at 1 hour at 60° C. was substantially the same as at 3 hours at 60° C. The yellow solid was milled with mortar and pestle to give 2.84 g of bazedoxifene ascorbate.

Purification 1

82 mg of the bazedoxifene ascorbate was dissolved in 1 mL of ethanol/water with some heat. The solution was precipitated by diethyl ether to give yellow amorphous powder.

Purification 2

To a few mg of bazedoxifene ascorbate was added isopropyl alcohol followed by a few drops of acetone. The resulting mixture was heated to 50° C. for 3-5 min to form a clear yellow solution. The solution was then cooled to about 4° C. to forming a yellow-brown precipitate (not crystalline).

Purification 3

About 1 g of bazedoxifene ascorbate was placed in conical flask and about 25 mL of acetone was added with mixing. A few drops (5 drops) of water were added with mixing to give a reddish-brown solution. Ether was added (about 15 mL) to precipitate the salt forming a cloudy, brown, gummy precipitate. Trituration with ether gave a brown precipitate (about 0.95 g). This brown fine solid was stored in a desiccator under vacuum at room temperature.

Example 2

Characterization of Bazedoxifene Ascorbate

Proton Nuclear Magnetic Resonance (H-NMR)

The proton NMR spectrum of bazedoxifene ascorbate prepared according to Example 1 in deuterated dimethyl sulfoxide (DMSO-$d_6$) was consistent with the structure of bazedoxifene ascorbate.

Mass Spectrum

Bazedoxifene ascorbate prepared according to Example 1 gave M+H: 471.3 (MW=470.3) for bazedoxifene; 2M+H: 941.6; M'+H: 177.1 for ascorbic acid.

High Performance Liquid Chromatography (HPLC)

Bazedoxifene ascorbate prepared according to Example 1 was analyzed by HPLC run under the following conditions:
Column: Prodigy ODS-2, 5 µm of 150 cm×4.6 mm
Detector: Ultraviolet (UV) at 220 nm
Column Temperature: 30° C.
Flow Rate: 1.5 mL/min
Mobile Phase: 680 mL of: 2 L of water containing 6.8 g monobasic potassium phosphate (adjusted to pH 3.0 with phosphoric acid); and 320 mL of acetonitrile.

The retention times for bazedoxifene and ascorbic acid were consistent with the structure.

Powder X-ray Diffraction (XRPD)

XRPD analyses were carried out on a Scintag X2 X-ray powder diffractometer using Cu Kα radiation. The tube power and amperage were set at 45 kV and 40 mA, respectively. The divergence and scattering slits were set at 1° and the receiving slit was set at 0.2 mm. The theta-two theta continuous scan at 3°/min (0.4 sec/0.02° step) from 3 to 40 °2θ was used. Samples were packed in a quartz sample holder.

Powder X-ray diffraction of bazedoxifene ascorbate prepared according to Example 1 showed an amorphous material.

Differential Scanning Calorimeter (DSC)

3.542 mg of bazedoxifene ascorbate prepared according to Example 1 were placed in PERKIN ELMER Pyris 1 DSC with autosampler and heated from 25° C. to 150° C. at a rate of 5° C./min. The output was measured in a sealed aluminum pan.

The material appeared to be amorphous with a glass transition (Tg) at 50.02° C.

Thermogravimetric Analysis (TGA)

1.377 mg of bazedoxifene ascorbate prepared according to Example 1 was placed in a PERKIN ELMER Pyris 1 TGA with an open sample pan flushed with nitrogen. The sample was scanned from 25° C. to 300° C. at a rate of 5° C./min.

The bazedoxifene ascorbate sample lost about 11% up to 100° C. (corresponding to about one molecule of water) and then another loss of weight occurred between 105° C. and 160° C.

Example 3

Equilibrium Solubility of Bazedoxifene Ascorbate in 0.0005 M Acetic Acid at 37° C.

Each of 10.1, 10.0, and 9.8 milligrams of bazedoxifene ascorbate, prepared according to Example 1, were put in 3 mL of 0.0005 M acetic acid and then placed in a water bath at 37° C. The samples were rotated at 50 rotation/min for 18 hours. All samples were filtered through 0.2 um (Nylon Acrodisc) filter. Samples were analyzed by HPLC.

The equilibrium solubility of bazedoxifene ascorbate was determined to be 1.66 mg/mL.

Example 4

Bulk Stability

A batch of bazedoxifene ascorbate prepared according to Example 1 was stored for a time in a vial on the bench top covered with aluminum foil. At 1 month and at 75 days, several mg were analyzed by HPLC. At the 1 month time point, HPLC showed 99.86% recovery. At the 75 day time point, HPLC showed 95.3% recovery.

Example 5

Bazedoxifene Ascorbate Solid Dispersion with PVP (1:1 w/w)

Preparation 0.5128 g of PVP K17 (PLASDONE C-15 "Povidone USP"; ISP Technologies, Inc.) was dissolved in 10 mL of ethanol. Then 0.5032 g of bazedoxifene ascorbate prepared according to Example 1 was added with magnetic stirring. The flask was flushed with nitrogen gas and put in a water bath at 70° C. for 10 minutes. The mixture turned clear brown solution and was left in the water bath without heating for 30 minutes. Solvents were evaporated under reduced pressure for 6 hours.

The resulting solid-glassy brown material was grinded with mortar and pestle to give brown-beige fine powder of 0.9244 g with a very good fluidity which did not solidify overnight.

The HPLC retention times and UV spectra were consistent with the composition of the dispersion. XRPD showed that the dispersion was amorphous. TGA revealed 2.7% weight loss up until about 100° C. believed to be due to loss of one molecule of water.

Example 6

Solubility of Bazedoxifene Ascorbate Solid Dispersion with PVP (1:1 w/w) in 0.0005 M acetic acid at 37° C.

Samples of bazedoxifene ascorbate solid dispersion of Example 5 (ca. 20 mg each) were placed in vials to which 1 mL of 0.0005 M acetic acid was added. The mixture was shaken by hand for 10 seconds and then placed in a water bath of 37° C. at 50 rotations/minute for 18 hours. The samples were then filtered through syringe disc filters (13 mm of 0.2 μm Nylon (Whatman)). Results: 12.364 mg/mL.

Example 7

Bulk Stability of Solid Dispersion

Bulk stability of bazedoxifene ascorbate solid dispersion with PVP (1:1 w/w) of Example 5 was assessed at 1 month and at 3 months according to the following procedure. Samples of 5-6 g of bazedoxifene ascorbate solid dispersion in vials wrapped with foil were placed on a benchtop at room temperature for one month or for three months. The samples were then analyzed by HPLC to give the following results:

Initial 44.79% (use at value);

1 month at room temperature: 43.14% (use at value);

3 month at room temperature: 44.44% (use at value).

Various modifications of the invention, in addition to those described herein, will be apparent to those skilled in the art from the foregoing description. Such modifications are also intended to fall within the scope of the appended claims. Each of the publications and, references, including books and patents, cited in the present application is incorporated herein by reference in its entirety.

What is claimed is:

1. An ascorbic acid salt of bazedoxifene.

2. A composition comprising the salt of claim 1 and a pharmaceutically acceptable carrier.

3. A method of preparing the salt of claim 1 comprising combining bazedoxifene free base and ascorbic acid.

4. The method of claim 3 wherein about equimolar amounts of bazedoxifene free base and ascorbic acid are combined.

5. The method of claim 3 wherein said combining is carried out in a solvent.

6. The method of claim 5 wherein said solvent comprises an alcohol.

7. The method of claim 6 wherein said alcohol comprises ethanol.

8. A salt prepared by the method of claim 3.

9. A solid dispersion comprising the salt of claim 1 and a dispersing agent.

10. The solid dispersion of claim 9 wherein said dispersing agent comprises a cellulose, hyaluronate, alginate, polysaccharide, heteropolysaccharide, poloxamers, poloxamines, ethylene vinyl acetate, polyethylene glycol, dextran, polyvinylpyrrolidone, chitosan, polyvinylalcohol, propylene glycol, polyvinylacetate, phosphatidylcholines, miglyol, polylactic acid, polyhydroxybutyric acid, mixture of two or more thereof or copolymer thereof.

11. The solid dispersion of claim 9 wherein said dispersing agent comprises polyvinylpyrrolidone.

12. The solid dispersion of claim 9 wherein the weight ratio of said salt to said dispersing agent is about 1:99 to about 99:1.

13. The solid dispersion of claim 9 wherein the weight ratio of said salt to said dispersing agent is about 1:99 to about 60:40.

14. The solid dispersion of claim 9 wherein the weight ratio of said salt to said dispersing agent is about 1:99 to about 10:90.

15. The solid dispersion of claim 9 wherein the weight ratio of said salt to said dispersing agent is about 5:95.

16. The solid dispersion of claim 9 wherein the weight ratio of said salt to said dispersing agent is about 40:60 to about 60:40.

17. The solid dispersion of claim 9 wherein the weight ratio of said salt to said dispersing agent is about 1:1.

18. A method of preparing the solid dispersion of claim 9 comprising:
    a) combining said salt and said dispersing agent in solution, wherein said solution comprises a solvent; and
    b) removing said solvent to yield said solid dispersion.

19. The method of claim 18 wherein said solvent is an organic solvent.

20. The method of claim 19 wherein said organic solvent comprises an alcohol.

21. The method of claim 20 wherein said alcohol comprises ethanol.

22. A solid dispersion prepared by the method of claim 18.

23. A method of preparing the solid dispersion of claim 9 comprising:
    a) combining said salt with melted dispersing agent to form a liquid mixture; and
    b) solidifying said liquid mixture to form said solid dispersion.

24. The method of claim 23 wherein said melted dispersing agent is prepared by heating said dispersing agent to a temperature above about 30° C.

25. The method of claim 23 wherein said solidifying comprises cooling said liquid mixture to a temperature at or below about 25° C.

26. A solid dispersion prepared by the method of claim 23.

27. A composition comprising the solid dispersion of claim 9 and a pharmaceutically acceptable carrier.

28. A method of lowering cholesterol in a mammal comprising administering to said mammal a therapeutically effective amount of the salt of claim 1.

29. A method of inhibiting bone loss in a mammal comprising administering to said mammal a therapeutically effective amount of the salt of claim 1.

30. A method of treating breast cancer in a mammal comprising administering to said mammal a therapeutically effective amount of the salt of claim 1.

31. A method of treating a postmenopausal woman for one or more vasomotor disturbances comprising administering to said postmenopausal woman a therapeutically effective amount of the salt of claim 1.

32. The method of claim 31 wherein said vasomotor disturbance is hot flush.

* * * * *